US 6,712,881 B2
(12) United States Patent
Hering et al.

(10) Patent No.: US 6,712,881 B2
(45) Date of Patent: Mar. 30, 2004

(54) CONTINUOUS, LAMINAR FLOW WATER-BASED PARTICLE CONDENSATION DEVICE AND METHOD

(75) Inventors: Susanne Vera Hering, Berkeley, CA (US); Mark Richard Stolzenburg, El Cerrito, CA (US)

(73) Assignee: Aerosol Dynamics Inc., Berkeley, CA (US)

( * ) Notice: Subject to any disclaimer, the term of this patent is extended or adjusted under 35 U.S.C. 154(b) by 0 days.

(21) Appl. No.: 10/354,419

(22) Filed: Jan. 30, 2003

(65) Prior Publication Data

US 2004/0020362 A1 Feb. 5, 2004

Related U.S. Application Data

(60) Provisional application No. 60/353,875, filed on Jan. 30, 2002.

(51) Int. Cl.$^7$ ................................................ B01D 49/00
(52) U.S. Cl. ........................ 95/228; 95/288; 96/243; 96/413; 62/617; 73/28.04; 73/863.12; 356/37; 356/339
(58) Field of Search .................... 95/288, 149, 227, 95/228; 96/243, 322, 413; 356/37, 339; 62/617; 73/28.05, 28.01, 28.04, 31.02, 31.03, 863.12, 863.21

(56) References Cited

U.S. PATENT DOCUMENTS

| 2,684,008 | A |   | 7/1954  | Vonnegut           |
|-----------|---|---|---------|--------------------|
| 3,694,085 | A |   | 9/1972  | Rich               |
| 3,806,248 | A |   | 4/1974  | Sinclair           |
| 4,449,816 | A |   | 5/1984  | Kohsaka et al.     |
| 4,790,650 | A |   | 12/1988 | Keady              |
| 4,950,073 | A |   | 8/1990  | Sommer             |
| 5,026,155 | A | * | 6/1991  | Ockovic et al.     |
| 5,118,959 | A |   | 6/1992  | Caldow et al.      |
| 5,239,356 | A |   | 8/1993  | Hollander et al.   |
| 5,519,490 | A | * | 5/1996  | Nakata et al.      |
| 5,659,388 | A |   | 8/1997  | Scheer et al.      |
| 5,675,405 | A |   | 10/1997 | Schildmeyer et al. |
| 5,699,679 | A | * | 12/1997 | Wu et al.          |
| 5,872,622 | A | * | 2/1999  | Schildmeyer et al. |
| 5,903,338 | A | * | 5/1999  | Mavliev et al.     |
| 6,230,572 | B1| * | 5/2001  | Pui et al.         |
| 6,330,060 | B1| * | 12/2001 | Flagan et al.      |
| 6,506,345 | B1| * | 1/2003  | Lee et al.         |
| 2002/0134137 | A1 | * | 9/2002 | Ondov et al.      |
| 2003/0020050 | A1 | * | 1/2003 | Heitzenberg et al.|

OTHER PUBLICATIONS

Aitken, "On the Number of Dust Particles in the Atmospher", Transaction of the Royal Society of Edinburgh, vol. XXXV, 1888.

Bricard, et al., "Detection Of Ultra–Fine Particles By Means Of A Continuous Flux Condensation Nuclei Counter", Proceedings of a symposium by U.S. Environmental Protection Agency held in Minneapolis, Minnesota, May 28–30, 1975.

(List continued on next page.)

*Primary Examiner*—Duane S. Smith
(74) *Attorney, Agent, or Firm*—Vierra Magen Marcus Harmon & DeNiro LLP

(57) ABSTRACT

An apparatus and method for producing a diffusive, continuous laminar flow for particle growth via condensation of vapors with a mass diffusivity near or higher than the thermal diffusivity of the surrounding gas. In an exemplary embodiment, the method uses the condensation of water vapor onto particles suspended in air.

58 Claims, 6 Drawing Sheets

OTHER PUBLICATIONS

Kousaka, et al., "Development of a Mixing Type Condensation Nucleus Counter", J. Aerosol Sci., vol. 13, No. 3, pp. 231–240, 1982.

Chuang, et al., "A theoretical analysis of cloud condensation nucleus (CCN) instruments", Journal of Geophysical Research, vol. 106, No. D4, pp. 3449–3474, Feb. 27, 2001.

Wang, et al., "Fast Mixing Condensation Nucleus Counter: Application to Rapid Scanning Differential Mobility Analyzer Measurements", Aerosol Sci. & Techn. 36:678–689, 2002.

Demokritou, et al., "A High Volume Apparatus for the Condensation Growth of Ultrafine Particles for Inhalation Toxicological Studies", Aerosol Sci & Techn. 36: 1061–1072, 2002.

Stolzenburg, et al., "An Ultrafine Aerosol Condensation Nucleus Counter", Aerosol Science and Technology 14: 48–65, 1991.

Hoppel, et al., "A Segmented Thermal Diffusion Chamber For Continuous Measurements of CN", J. Aerosol Sci., vol. 10, pp. 369–373, 1979.

* cited by examiner

CONTINUOUS, LAMINAR FLOW WATER-BASED PARTICLE CONDENSATION DEVICE AND METHOD

PRIORITY DATA

The present application claims priority to U.S. Provisional Patent Application No. 60/353,875, filed Jan. 30, 2002, entitled "Continuous, Laminar Flow, Water-Based Particle Condensation Device."

BACKGROUND OF THE INVENTION

1. Field of the Invention

The present invention is directed to the measurement of airborne particles and aerosols through condensational growth.

2. Description of the Related Art

Airborne particles are ever present in the environment. Microscopic particles in the air include soil, smoke, photochemical, salt, dusts, fumes, mists, smog, and atmospheric water or ice particles. The presence of these particulates affects visibility, climate, health and quality of life. These airborne particles are examples of aerosols. Aerosols are generally defined as solid or liquid particles suspended in a gas.

Many measurement methods for aerosol particles rely on condensational growth to enlarge particles to a size that can be detected by optical or other means. Condensational growth is also used to enable the collection of particles for chemical analysis. One type of particle measurement device is commonly referred to as a condensation particle counter (CPC). CPCs specifically examine the number concentration of particles that increase in size by condensational growth. This growth results from supersaturation of a condensing vapor in the surrounding gas. The saturation ratio is defined as the partial pressure of a vapor over its saturation vapor pressure. The saturation vapor pressure is the pressure required to maintain a vapor in mass equilibrium with the condensed vapor (liquid or solid) at a specified temperature. Supersaturation refers to that portion of the saturation ratio greater than 1.0.

According to this method, particles grow using a supersaturated vapor to a sufficiently large size for easy detection and quantification by optical methods. The aerosol is first exposed to the vapor of a working fluid (such as butanol, alcohol, or water) in a saturation chamber. Subsequently, vapor condensation onto particles is induced by either adiabatic expansion or cooling in the condensing chamber, or by mixing with a cooler airflow. The formed droplets are then detected using light scattering or attenuation techniques.

CPCs suffer from two general issues: low flow rates and the use of toxic chemicals as working fluids.

The earliest detectors saturated an air sample with water vapor, and then expanded the air adiabatically to produce cooling and subsequent condensation onto the particles. (J. Aitken: On the number of dust particles in the atmosphere, Proc. Royal Soc. Edinburgh 35, 1888).

An automated condensation particle counter using this principal was disclosed in U.S. Pat. No. 2,684,008. This was a semi-continuous instrument that cycled between the sample and expansion modes. Another design, disclosed in U.S. Pat. No. 3,694,085, shows an automatic, semi-continuous counter that used mixing to cool and condense.

Continuous, laminar flow condensation particle counters pass the sample air flow through a saturator and then through a condenser. The saturator mixes the air with a condensable vapor such as butanol. From the saturator the air passes into a condenser tube that is cooler than the saturator. The cooling of the airflow within the condenser creates a supersaturation region and results in condensational growth of the suspended particles such that they can be counted optically. (See, J. Bricard, P. Delattre, G. Madelaine and M. Pourprix in Fine Particles, B. Y. H. Liu, editor, Academic Press, NY, 1976, pp 565–580; U.S. Pat. No. 3,806,248). This approach has been used extensively for particle number concentration measurement. Many have refined the method through use of a plurality of streams, improved saturator design, or temperature control.

Current continuous, laminar flow particle condensation instruments use cooled-wall condensers. The devices create supersaturation because, in part, the thermal diffusivity of the gas is greater than the mass diffusivity of the condensing vapor. Condensation is achieved by cooling the flow such that the temperature drops more quickly than the condensing fluid can diffuse, thereby creating a region of supersaturation. Particles within this supersaturation region will grow by condensation. These systems do not work well for particles suspended in air when the condensing fluid is water. With water the degree of supersaturation achieved is small because the water vapor diffuses too quickly, before the temperature of the sample stream is lowered.

Hence, these systems are typically operated with butanol, which has a vapor mass diffusivity of 0.081 cm2/s. (The mass diffusivity for water vapor is more than three times higher, 0.265 cm2/s.) The thermal diffusivity of air, which determines the rate of heat transfer, is 0.215 cm2/s.

Yet, for many applications, it is desirable to use water as the condensing fluid. Water is nontoxic and inexpensive. Water-based condensation counters would be suitable for measurements in offices, homes and other inhabited locations. They present less of a problem for operation in clean rooms, such as those used for microchip manufacture. Water is preferred over butanol or other fluids when collecting particles for chemical analysis.

Early counters used water as the condensing substance, but were not continuous. (See, J. Aitken: *On the number of dust particles in the atmosphere*, Proc. Royal Soc. Edinburgh 35, 1888; U.S. Pat. Nos. 2,684,008 and 3,694,085). Alternative designs, such as that disclosed in U.S. Pat. No. 4,449,816, show a continuous condensation counter that may be used with water based on the mixing of two saturated fluids with differing temperatures. Yet another design, shown in U.S. Pat. No. 6,330,060, discloses a continuous flow cloud condensation nucleus counter that employs a segmented condenser, with alternating hot and cold rings to Droduce well-controlled, albeit low, sudersaturation (See also, W. A. Hoppel, S. Twomey and T. A. Wojchiechowski (J. Aerosol Sci 10: 369–373, 1979).

Hence, a continuous flow device having a high flow rate and using non-toxic chemicals would be useful.

SUMMARY OF THE INVENTION

The present invention, roughly described, pertains to a method for enlarging particles by condensation. The method may be utilized in the detection, counting or other analysis of particles in aerosols. The method includes the steps of: introducing a particle-laden flow at a first temperature; and passing the flow through a condenser having a second temperature greater than the flow and a vapor pressure of a condensing vapor at walls of the condenser near saturation. In a further aspect, the condensing fluid is water.

In another embodiment, the invention is a method comprising the steps of: forming a particulate sample at a first temperature; and passing the particulate sample through a wet walled chamber including interior walls provided at a second temperature greater than the first temperature, and wherein a condensing fluid is near its saturation vapor pressure at the walls.

In yet another embodiment, the invention is a particle condensation apparatus. The apparatus includes an inlet receiving an aerosol flow, and a preconditioner coupled to the inlet and having a first temperature, the preconditioner having an outlet. A condenser is coupled to the outlet of the preconditioner and receives the aerosol flow from the preconditioner. The condenser has interior walls provided at a second temperature higher than the first temperature. This difference in temperature may be achieved by cooling the flow in the preconditioner or by heating the condenser, or by a combination of both. In a further aspect, the condenser is tubular in shape. In yet another aspect, the condensing vapor in the apparatus has a vapor pressure at the interior walls which is near saturation.

In another embodiment, the invention comprises a particle condensation apparatus. The apparatus includes a sample inlet receiving a particle laden airflow having a first temperature, and a condenser having interior walls provided at a second temperature higher than the first temperature and having a wet surface. In unique embodiments, the second temperature is 15° C. or greater than the first temperature, 25° C. or greater than the first temperature and 45° C. or greater than the first temperature.

These and other objects and advantages of the present invention will appear more clearly from the following description in which the preferred embodiment of the invention has been set forth in conjunction with the drawings.

BRIEF DESCRIPTION OF THE DRAWINGS

The invention will be described with respect to the particular embodiments thereof. Other objects, features, and advantages of the invention will become apparent with reference to the specification and drawings in which.

DETAILED DESCRIPTION

This invention comprises an apparatus and method for producing a diffusive, continuous laminar flow for particle growth via condensation of vapors with a mass diffusivity near or higher than the thermal diffusivity of the surrounding gas. In an exemplary embodiment, the method uses the condensation of water vapor onto particles suspended in air.

In general the invention makes use of a warm, wet-walled condenser.

Figure 1A:
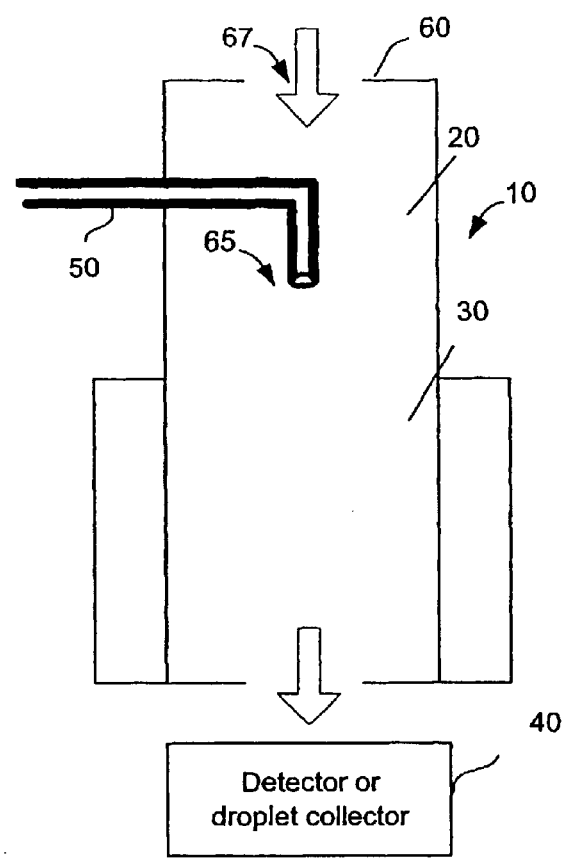
FIG. 1A depicts a first embodiment of an apparatus suitable for use in the present invention.
Figure 1B:
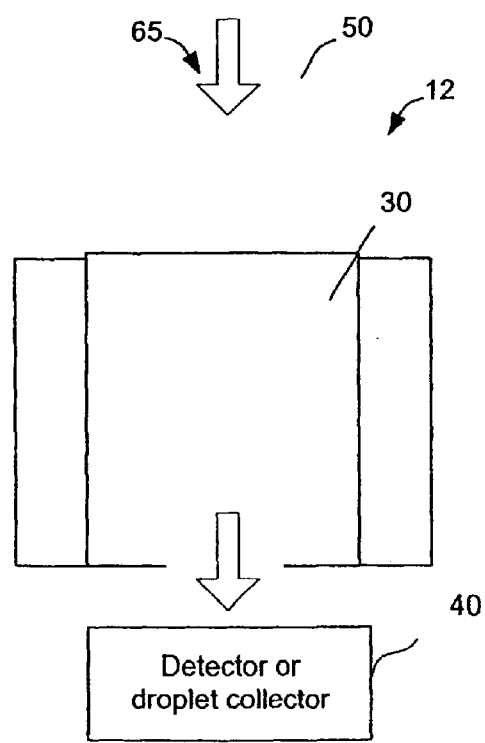
FIG. 1B depicts a second embodiment of an apparatus suitable for use in the present invention.

FIG. 1A shows a first embodiment of the apparatus of the invention. The apparatus includes a preconditioner 20, a condenser 30, a filtered air input 60 and an aerosol sample inlet 50. The condenser has at least one interior wall which may, in one embodiment, be formed in a tubular configuration. The output of the condenser is coupled to a detector or droplet collector 40. In one embodiment, the detector is an optical detector such as that shown in U.S. Pat. Nos. 4,790,650 and 5,239,356, or instruments sold by TSI Inc. (model nos. 3760, 3025). An alternative embodiment of the invention is shown in FIG. 1B. In this embodiment, the apparatus 12 is similar to the apparatus 10 of FIG. 1A, but the sheath flow and/or saturator may be eliminated. Operation of the device of the present invention requires only that the temperature of the air stream entering the condenser is colder than the walls of the condenser. It does not require that the airstream entering the condenser be saturated. If the application permits the use of a sufficiently high condenser wall temperature, the preconditioner will not be needed. Alternatively, the air stream may be preconditioned to a desired temperature. The physical geometry of the apparatus 10 and 12 are similar to prior art continuous, laminar flow condensation counters. However, a fundamental difference is that the temperature of the walls of the condenser 30 is higher than that of the entering air stream 65 (FIG. 1B) or the walls of the preconditioner 20 (FIG. 1A) In addition the vapor pressure of the condensing vapor at the walls of the condenser is near saturation (e.g., within 10% of its saturation vapor pressure). This may be achieved by wetted walls. In this context, the term “wetted” means walls that are coated with the condensed vapor.

In accordance with the process of the invention, a particle-laden stream 65 is introduced into a condenser tube 30 whose walls are warm and saturated with water or other condensable vapor. A particle-free sheath stream 67 may be introduced via inlet 60. The sheath stream may be provided at a desired temperature or the preconditioner may condition the sheath stream and particle stream 65 to the desired temperature prior to entering the condenser. In one aspect, the preconditioner may be a saturator. However, any device which changes the temperature of the sample or sheath flow may be considered a preconditioner in the context of the invention.

Prior art instruments rely on cooling to produce the supersaturation. In contrast, the method and apparatus of the present invention utilize the fact that the mass diffusivity of water vapor exceeds the thermal diffusivity of air. Thus, when colder air is introduced into a warmer chamber with wetted walls, the diffusion of water vapor from the walls into the flow is faster than the heating of the flow. This difference produces a maximum supersaturation along the centerline of the flow.

Performance of the invention can be characterized by the efficiency of activation of condensational growth on particles as a function of particle diameter, $D_p$:

$\eta_{act}(D_p)$=fraction of particles of diameter $D_p$ entering condenser on which vapor is condensed.

Generally, the smaller the particle the more difficult it is to condense vapor on it, and for any device, there is a smallest particle size which can be activated for condensational growth.

Activation efficiencies, $\eta_{act}(D_p)$, are predicted from a two-dimensional model of convective and diffusive heat and mass transfer in the condenser. Profiles of temperature, T, throughout the condenser are obtained by solution of the partial differential equation, $$2U[1-(r/R)^2]\frac{\partial T}{\partial z} = \alpha_t \cdot \frac{1}{r}\frac{\partial}{\partial r}\left(r\frac{\partial T}{\partial r}\right)$$

where r and z are radial and axial coordinates, respectively, R is tube radius, U is average flow velocity and $\alpha_t$ is thermal diffusivity of the flowing gas. A fully-developed parabolic flow profile is assumed with piecewise-uniform entering temperature profile and uniform wall temperature. Fluid properties evaluated at a mean temperature are treated as constants over the domain. Axial thermal diffusion (conduction) and other second order effects such as Stefan flow are ignored. Similar equations determine the partial pressure, $p_v$, of the water vapor and the size-dependent particle concentration, $N(D_p)$, replacing at with vapor diffusivity, $D_v$, and size-ependent particle diffusivity, $D(D_p)$, respectively. At the condenser wall the vapor is assumed to be saturated and the particle concentration zero.

These three independent boundary value problems each take the form of the classic Graetz problem. Each can be solved by separation of variables and each of the three profiles expressed in the form of the standard series solution to the Graetz problem. In this work, the first twenty terms with their corresponding eigenvalues and eigenfunctions are used in each series.

The profile for the water vapor saturation ratio, $$S = p_v / p_{sat}(T),$$

is obtained from the T and $p_v$ profiles where $p_{sat}(T)$ is the saturation water vapor pressure at temperature T. Associated with S at any point is the equilibrium Kelvin diameter, $$D_{k,eq} = (4\sigma_s M_w)/(\rho_1 RT \cdot \log S),$$

where $M_w$, $\rho_1$ and $\sigma_s$ are the molecular weight, liquid density and surface tension of water, R is the universal gas constant and T is the absolute temperature. $D_{k,eq}$ is a property of water and is equal to the diameter of a liquid water droplet in equilibrium with water vapor at saturation ratio S and temperature T. The Kelvin equivalent diameter, $D_k$, of any particle is equal to the $D_{k,eq}$ associated with the saturation ratio which just activates condensation on the particle. Particles with $D_k$ greater than $D_{k,eq}$ are activated and grow; smaller particles are not. The overall minimum $D_{k,eq}$ is located at a point some distance along the condenser centerline. Contours of constant $D_{k,eq}$ expand about this point as $D_{k,eq}$ increases.

Activation efficiency is determined by the fraction of particles of size $D_k$ traversing the condenser which intersect the $D_{k,eq} = D_k$ contour. Each contour has a point of maximum radial cross section. Activation efficiency, $\eta_{act}(D_p)$, is calculated as the fraction of particles of size $D_p = D_{k,eq}$ (assuming $D_p = D_k$) which pass through this cross section. It is found by integrating the Graetz solution for the particle concentration profile, $N(D_p)$, over this cross section.

Calculations have been performed using the geometry of the ultrafine condensation particle counter designed by M. Stolzenburg and P. McMurry (Aerosol Science and Technology 14: 48–65 (1991)). The basic arrangement is shown in FIG. 1A. Calculations were done for the conventional configuration, with a cooled-wall condenser, and for the warm, wet-walled condenser, and the results are shown in Tables 1 and 2. Both configurations have a saturator as a preconditioner. Tables 1 and 2 show the maximum saturation ratio achieved along the centerline of the flow, where the saturation is defined as the ratio of the actual vapor concentration to the equilibrium vapor concentration. For the conventional, cooled-wall condenser, a high saturation ratio along the centerline is achieved with butanol, but not with water. With water as the condensing fluid, the maximum centerline saturation ratio achieved with the conventional configuration is 1.15. For the warm wet-walled condenser of the present invention, one can achieve a ratio of 1.69 by simply switching the temperatures of the condenser and saturator. For a more optimal temperature of 51° C. for the condenser, with 10° C. in the saturator, one can achieve a saturation ratio in the condenser of 2.18.

TABLE 1

Conventional Cooled-wall Condenser

| CONDENSING FLUID | SATURATOR TEMPERATURE | CONDENSER TEMPERATURE | MAXIMUM CENTERLINE SUPER-SATURATION RATIO |
|---|---|---|---|
| Butanol | 41° C. | 10° C. | 3.61 |
| Water | 41 | 10 | 1.15 |

TABLE 2

Warm, Wet-Wall Condenser

| CONDENSING FLUID | SATURATOR TEMPERATURE | CONDENSER TEMPERATURE | MAXIMUM CENTERLINE SUPER-SATURATION RATIO |
|---|---|---|---|
| Water | 10° C. | 41° C. | 1.69 |
| Water | 10 | 51 | 2.18 |

Figure 4:
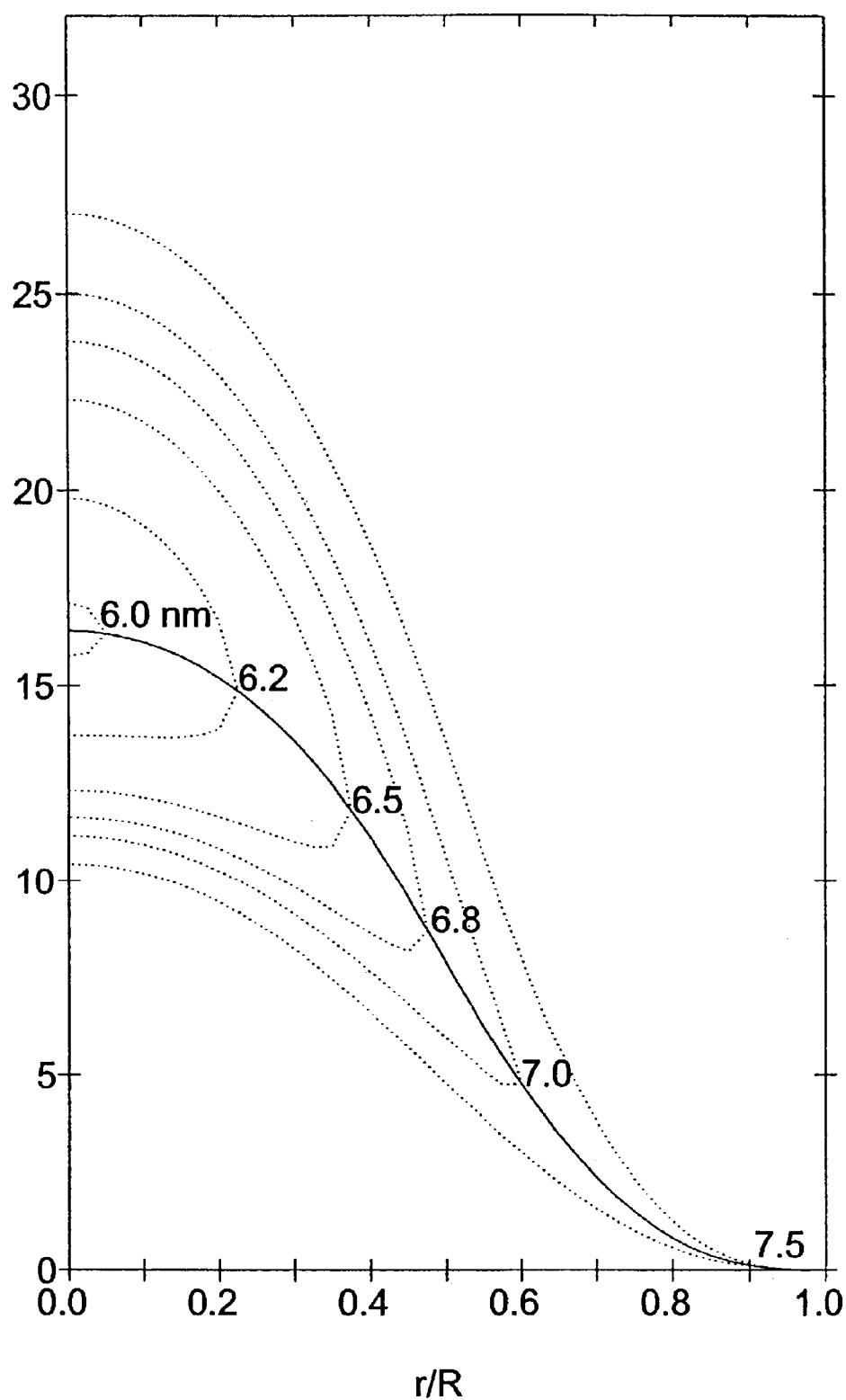
Figure 5:
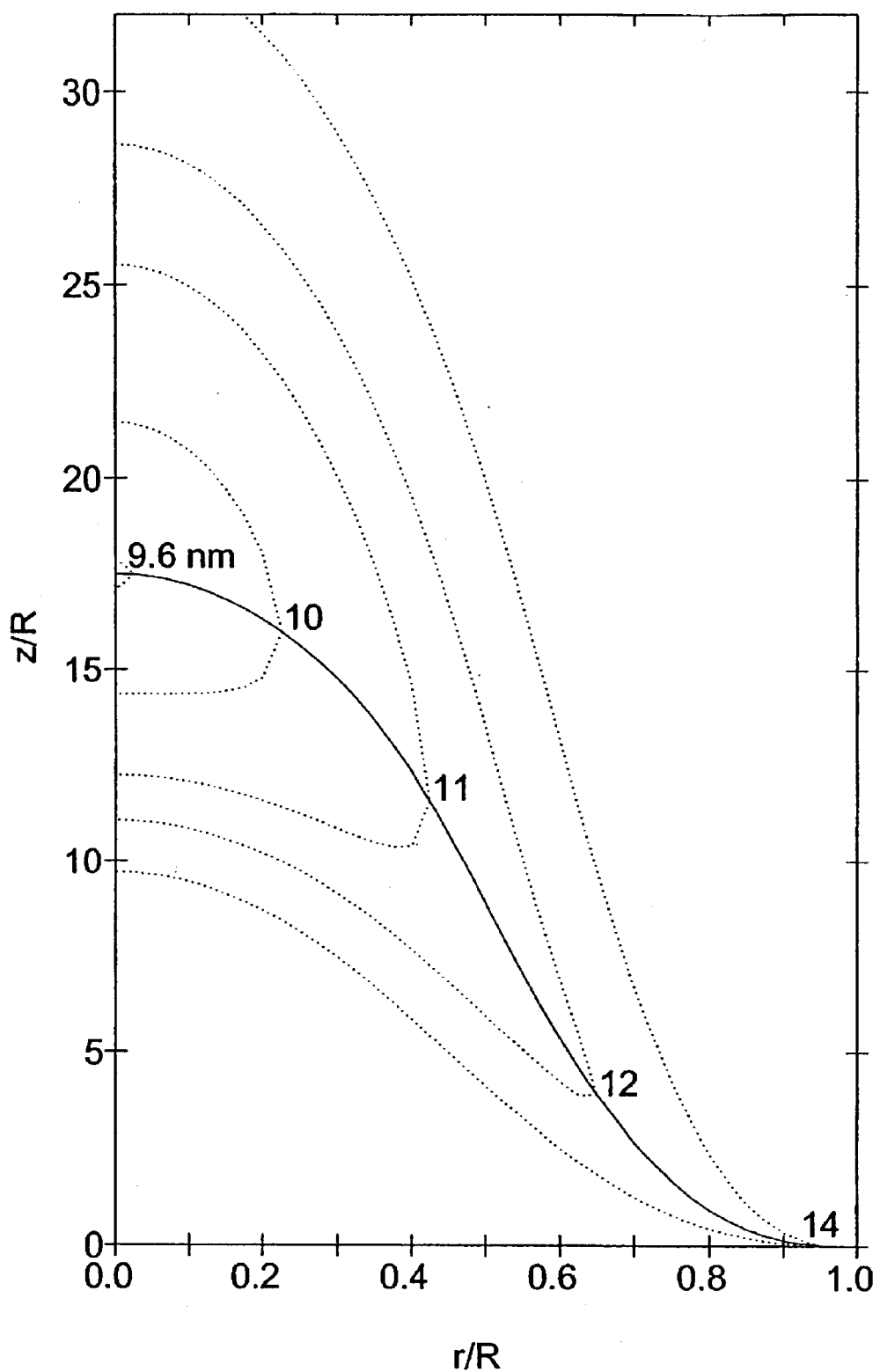
Figure 6:
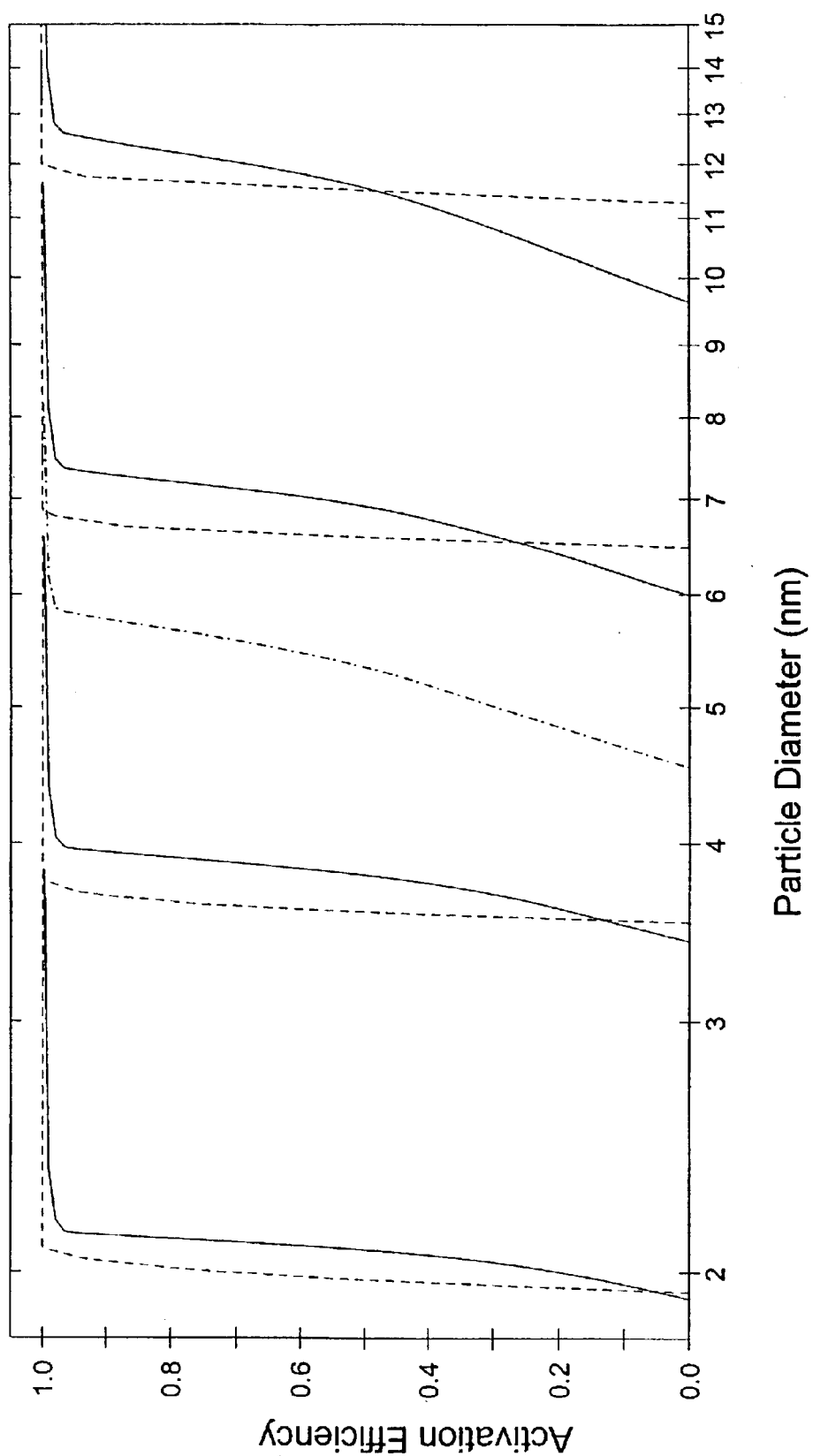
FIG. 6 is a graph showing the activation efficiencies for the systems described with respect to FIGS. 2 through 5.

Contours of constant $D_{k,eq}$ for several possible condenser configurations are shown in FIGS. 2–5 with corresponding activation efficiency curves, $\eta_{act}(D_p)$, shown in FIG. 6. These are all for systems using air as the carrier gas and water as the condensable vapor. The condenser tube has an inner diameter of 0.25 inch with a total flow rate through it of 1.0 liter per minute at atmospheric pressure.

Figure 2:
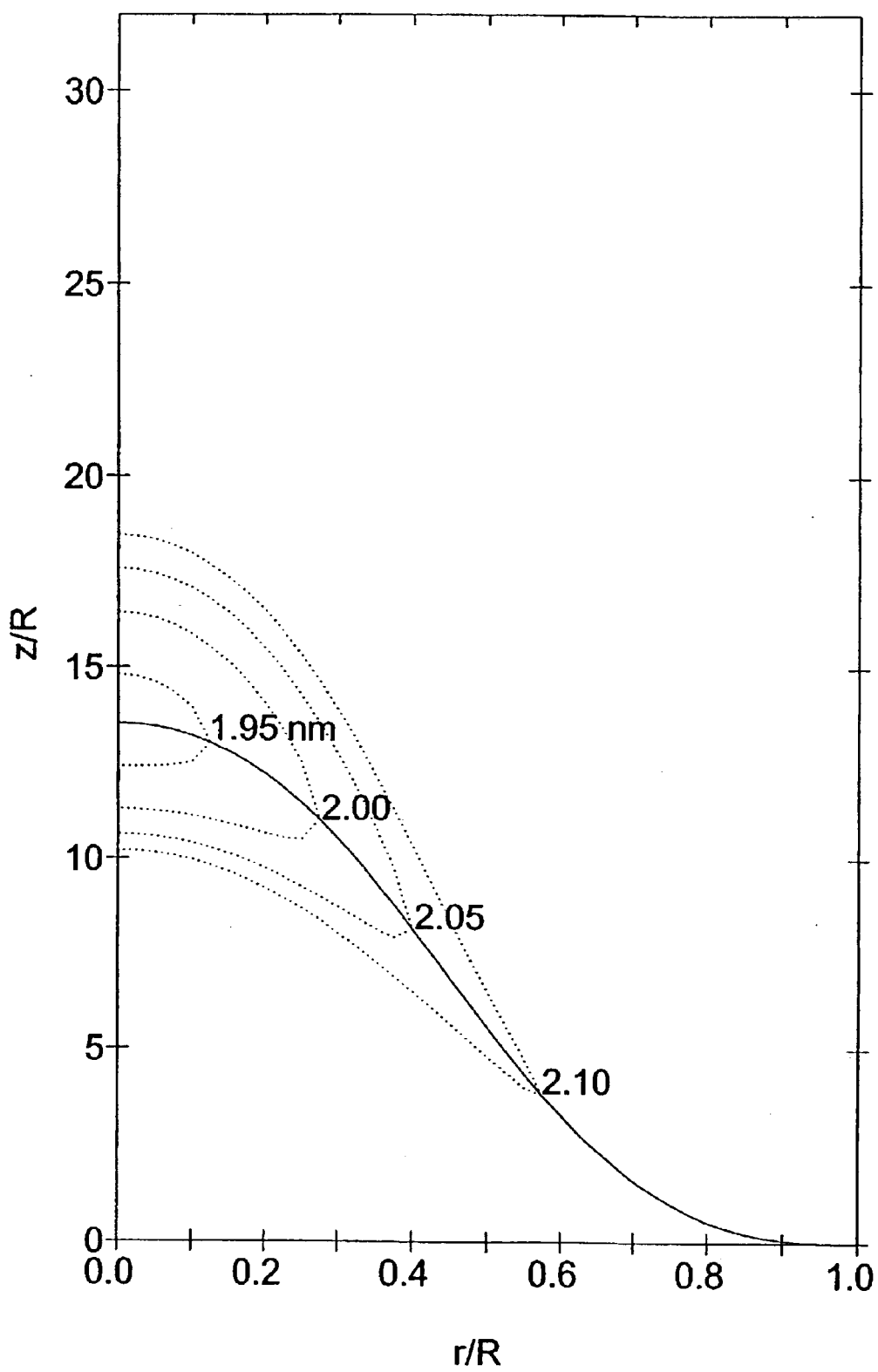
FIGS. 2 through 5 are graphs showing condensation profiles for various embodiments of the present invention.
Figure 3:
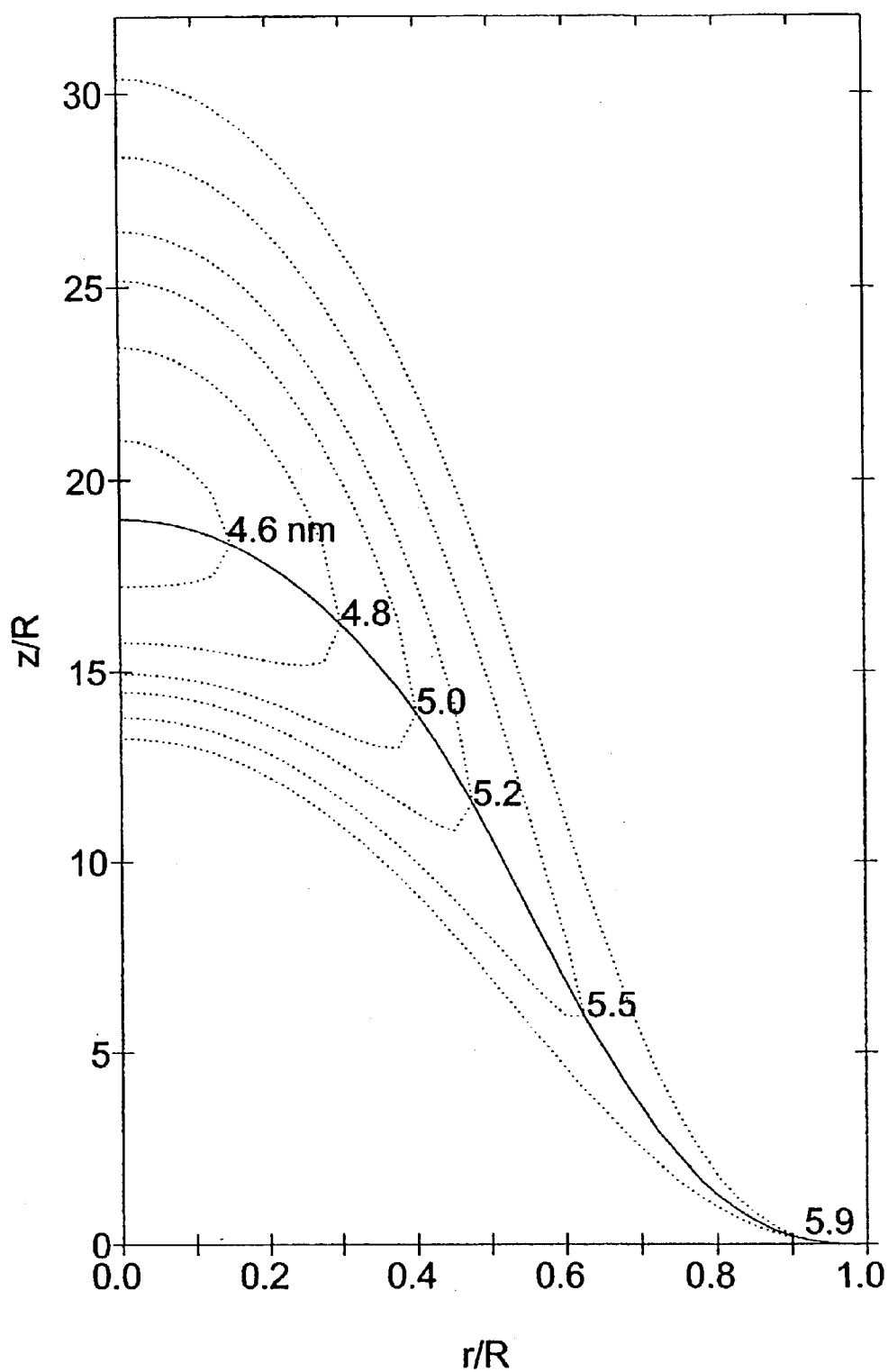

FIG. 2 shows a graph of supersaturation profiles within the warm, wet-walled condenser for a system with a particle-laden aerosol flow surrounded by a particle-free sheath flow as in FIG. 1A. The radial distance (r) is normalized with respect to the tube radius (R), with a value of 0 indicating the centerline. The nondimensional axial distance (z) is the distance down the length of the condenser, measured in radii. Contours correspond to lines of equal supersaturation. The value of the supersaturation is indicated by the smallest particle size $D_{k,eq}$ that is activated at the calculated supersaturation ratio. The larger the supersaturation, the smaller the particle size that is activated.

The flow entering the condenser is at temperature $T_{in}$=10° C. and the temperature at the condenser wall is $T_{con}$=65° C. The distance from where the aerosol and sheath flows merge to the entrance of the condenser tube is 1.0 inch. The entering sheath flow is saturated with water vapor at $T_{in}$ but the entering aerosol flow has no water vapor for these model calculations. (In practice, the aerosol flow may enter at anywhere from 0 to 100% relative humidity but this has relatively little effect on these model calculations. Any water vapor in the entering aerosol flow will improve the performance slightly.)

As shown in FIG. 2, with the warm, wet-walled condenser, the supersaturation ratio reaches 2.92, which activates particles with a diameter of 1.94 nm. This profile is very similar to that calculated by Stolzenburg for an ultrafine condensation counter (M. Stolzenburg and P. McMurry (Aerosol Sci and Technology 14: 48–65, 1991) that operates with butanol and a cooled wall condenser, wherein this theory matched experimental data.

FIGS. 3, 4 and 5 are profiles for systems with no sheath flow, such as in the embodiment in FIG. 1B. In FIG. 3, $T_{in}$=100° C., $T_{con}$=46.5° C., and the entering aerosol flow is dry. In FIG. 4, $T_{in}$=10° C., $T_{con}$=35° C. and the entering aerosol flow is saturated. In FIG. 5, $T_{in}$=250° C., $T_{con}$=45° and the entering aerosol flow is saturated.

FIG. 6 shows the activation efficiencies for these same systems as well as for similar systems with the same temperatures, for both sheathed or unsheathed systems. Dashed lines are for sheathed systems with saturated entering sheath flows and dry entering aerosol flows. Solid lines are for unsheathed systems with saturated entering aerosol flows. The dot-dashed line is for the unsheathed system of FIG. 3 with dry entering aerosol flow. Starting from the left side of FIG. 6, the first two curves are for the temperatures of FIG. 2, the next three curves are for the temperatures of FIG. 3, the next two curves are for the temperatures of FIG. 4 and the last two curves are for the temperatures of FIG. 5. As in the ultrafine condensation counter of Stolzenburg and McMurry, discussed above, the system of the present invention produces a well defined supersaturation to which the particles are exposed. These figures show improved performance with greater temperature difference, with presaturation of the entering flow and with sheathing with particle-free air.

Several additional considerations may be taken into account in the optimization of this design. The system may be operated in a horizontal or vertical design, however, a vertical configuration generally will minimize disruption of the flow from natural convection. In one embodiment, the flow may be directed downwards; in another embodiment, the flow may be directed upwards. The system may be operated with or without sheath flow provided at inlet 60. With sheath flow, particles are only introduced along the centerline of the flow.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention to be defined by the claims appended hereto.

What is claimed is:

1. A method for enlarging particulate, comprising:

introducing a particle laden flow at a first temperature into a condenser; and passing the flow through the condenser having a second temperature greater than the flow wherein a vapor pressure of a condensing vapor at walls of the condenser is near saturation.

2. The method of claim 1 wherein the condensing vapor is water.

3. The method of claim 1 wherein the condensing vapor is methanol.

4. The method of claim 1 wherein the step of passing the flow includes passing the flow through the condenser wherein interior walls of the condenser are wet.

5. The method of claim 1 wherein the step of introducing includes introducing the particle-laden gas flow surrounded by a particle-free sheath flow.

6. The method of claim 5 wherein the step of introducing includes conditioning a temperature and vapor pressure of the particle-free sheath flow.

7. The method of claim 1 wherein the step of introducing includes conditioning a temperature and vapor pressure of the particle-laden flow.

8. The method of claim 5 wherein the step of introducing includes conditioning as temperature of the particle-free sheath flow.

9. The method of claim 1 wherein the step of introducing includes conditioning as temperature of the particle-laden flow.

10. The method of claim 5 wherein the particle-free sheath flow is air.

11. The method of claim 5 wherein the particle-free sheath flow is nitrogen.

12. The method of claim 1 wherein the particle laden flow includes air.

13. The method of claim 1 wherein the particle laden flow includes nitrogen.

14. The method of claim 5 wherein a mass diffusivity of the condensable vapor is higher than a thermal diffusivity of the particle-free sheath flow.

15. The method of claim 1 wherein a mass diffusivity of the condensable vapor is higher than a thermal diffusivity of the particle-laden flow.

16. The method of claim 5 wherein the step of introducing comprises actively cooling the particle-free sheath flow such that the first temperature is at least 15° C. lower than the second temperature.

17. The method of claim 5 wherein the step of introducing comprises actively cooling the particle-free sheath flow such that the first temperature is at least 25° C. lower than the second temperature.

18. The method of claim 5 wherein the step of introducing comprises actively cooling the particle-free sheath flow such that the first temperature is at least 45° C. lower than the second temperature.

19. The method of claim 1 further including the step of detecting droplets formed in the condenser by an optical detector.

20. The method of claim 1 further including the step of detecting droplets formed in the condenser by a droplet collection device.

21. The method of claim 1 further including the step of analyzing the chemical composition of the particles.

22. The method of claim 1 wherein the step of introducing comprises actively cooling the flow such that the first temperature is at least 15° C. lower than the second temperature.

23. The method of claim 1 wherein the step of introducing comprises actively cooling the flow such that the first temperature is at least 25° C. lower than the second temperature.

24. The method of claim 1 wherein the step of introducing comprises actively cooling the flow such that the first temperature is at least 45° C. lower than the second temperature.

25. A method, comprising:

forming a particulate sample at a first temperature; and passing the particulate sample through a chamber including interior walls provided at a second temperature greater than the first temperature, and wherein a condensing fluid is near its saturation vapor pressure at the walls.

26. The method of claim 25 wherein the second temperature is 15° C. or greater than the temperature of the entering gas flow.

27. The method of claim 25 wherein the second temperature is 25° C. or greater than the temperature of the entering gas flow.

28. The method of claim 25 wherein the second temperature is 45° C. or greater than the temperature of the entering gas flow.

29. The method of claim 25 wherein the condensing fluid is water.

30. The method of claim 25 wherein the condensing fluid is methanol.

31. The method of claim 25 wherein the step of forming is performed in a pre-conditioner.

32. The method of claim 25 wherein the step of passing includes introducing the particle-laden gas flow surrounded by a particle-free sheath flow.

33. The method of claim 32 wherein the particle-free sheath flow is air.

34. The method of claim 32 wherein the particle-free sheath flow is nitrogen.

35. The method of claim 25 further including the step of detecting, collecting or focusing droplets formed in the condenser.

36. A particle condensation apparatus, comprising:
an inlet receiving an aerosol flow;
a preconditioner having a first temperature and being coupled to the inlet, the preconditioner having an outlet; and
a condenser coupled to the outlet and receiving the aerosol flow from the preconditioner, the condenser having interior walls provided at a second temperature higher than the first temperature and including a condensing vapor having a vapor pressure at the interior walls which is near saturation.

37. The particle condensation apparatus of claim 36 wherein the condenser is tubular in shape.

38. The method of claim 36 wherein the condensing vapor is water.

39. The method of claim 36 wherein the condensing vapor is methanol.

40. The particle condensation apparatus of claim 36 further including a particle-free sheath flow inlet to the apparatus.

41. The particle condensation apparatus of claim 40 wherein the first temperature and a vapor pressure of the particle-free sheath flow are controlled by the preconditioner.

42. The particle condensation apparatus of claim 36 wherein the first temperature and a vapor pressure of the particle-laden flow are controlled by the preconditioner.

43. The particle condensation apparatus of claim 40 wherein a temperature of the particle-free sheath flow is controlled by the preconditioner.

44. The particle condensation apparatus of claim 36 wherein a temperature of the particle-laden flow is controlled by the preconditioner.

45. The particle condensation apparatus of claim 40 wherein the particle-free sheath flow is air.

46. The particle condensation apparatus of claim 40 wherein the particle-free sheath flow is nitrogen.

47. The particle condensation apparatus of claim 36 further including an optical device for detecting particulate exiting the condenser.

48. The particle condensation apparatus of claim 36 further including a droplet collection device.

49. A particle condensation apparatus, comprising:

an air inlet receiving a particle laden airflow; and a condenser having interior walls provided at a temperature higher than a temperature of the airflow into the condenser and having a wet surface.

50. The particle condensation apparatus of claim 49 wherein the second temperature is 15° C. or greater than the first temperature.

51. The particle condensation apparatus of claim 49 wherein the second temperature is 25° C. or greater than the first temperature.

52. The particle condensation apparatus of claim 49 wherein the second temperature is 45° C. or greater than the first temperature.

53. The particle condensation apparatus of claim 49 further including a particle-free sheath flow inlet to the apparatus.

54. The particle condensation apparatus of claim 53 wherein the particle free sheath flow is at least 15° C. lower than the second temperature.

55. The particle condensation apparatus of claim 53 wherein the particle free sheath flow is at least 25° C. lower than the second temperature.

56. The particle condensation apparatus of claim 53 wherein the particle free sheath flow is at least 35° C. lower than the second temperature.

57. The particle condensation apparatus of claim 36 further including an optical device for detecting particulate exiting the condenser.

58. The particle condensation apparatus of claim 36 further including a droplet collection device.

* * * * *

UNITED STATES PATENT AND TRADEMARK OFFICE
CERTIFICATE OF CORRECTION

PATENT NO. : 6,712,881 B2
DATED : March 30, 2004
INVENTOR(S) : Hering

It is certified that error appears in the above-identified patent and that said Letters Patent is hereby corrected as shown below:

Column 8,
Line 2, after "conditioning" before "temperature" is the word -- a --
Line 5, after "conditioning" before "temperature" is the word -- a --

Signed and Sealed this

Fifth Day of April 2005

JON W. DUDAS
*Director of the United States Patent and Trademark Office*

(12) EX PARTE REEXAMINATION CERTIFICATE (10142nd)
United States Patent
Hering et al.

(10) Number: US 6,712,881 C1
(45) Certificate Issued: May 2, 2014

(54) CONTINUOUS, LAMINAR FLOW WATER-BASED PARTICLE CONDENSATION DEVICE AND METHOD

(75) Inventors: Susanne Vera Hering, Berkeley, CA (US); Mark Richard Stolzenburg, El Cerrito, CA (US)

(73) Assignee: Aerosol Dynamics Inc., Berkeley, CA (US)

Reexamination Request:
No. 90/012,871, May 21, 2013

Reexamination Certificate for:
Patent No.: 6,712,881
Issued: Mar. 30, 2004
Appl. No.: 10/354,419
Filed: Jan. 30, 2003

Certificate of Correction issued Apr. 5, 2005

Related U.S. Application Data

(60) Provisional application No. 60/353,875, filed on Jan. 30, 2002.

(51) Int. Cl.
*G01N 15/06* (2006.01)

(52) U.S. Cl.
CPC .................................. *G01N 15/065* (2013.01)
USPC ................... 95/228; 95/288; 96/243; 96/413; 62/617; 73/28.04; 73/863.12; 356/37; 356/339

(58) Field of Classification Search
None
See application file for complete search history.

(56) References Cited

To view the complete listing of prior art documents cited during the proceeding for Reexamination Control Number 90/012,871, please refer to the USPTO's public Patent Application Information Retrieval (PAIR) system under the Display References tab.

*Primary Examiner* — Timothy Speer

(57) ABSTRACT

An apparatus and method for producing a diffusive, continuous laminar flow for particle growth via condensation of vapors with a mass diffusivity near or higher than the thermal diffusivity of the surrounding gas. In an exemplary embodiment, the method uses the condensation of water vapor onto particles suspended in air.

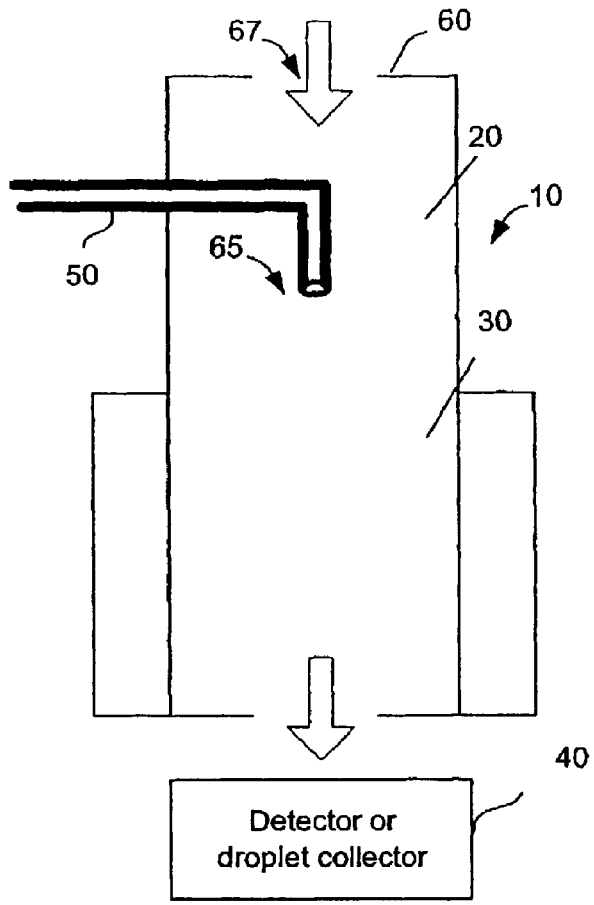

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 25, 36, 38-46 and 49-58 are determined to be patentable as amended.

Claims 2-24, 26-35, 37, 47 and 48, dependent on an amended claim, are determined to be patentable.

1. A method for enlarging particulate, comprising:
introducing a particle laden flow at a first temperature into a condenser; and
passing the flow through [a] *the* condenser having a second temperature greater than the flow wherein a vapor pressure of a condensing vapor at walls of the condenser is near saturation *and operating the condenser such that the flow through the condenser is laminar*.

25. A method, comprising:
forming a particulate sample at a first temperature; and
passing the particulate sample through a chamber including interior walls provided at a second temperature greater than the first temperature *in a manner such that a flow of the sample in the chamber is laminar*, and wherein a condensing fluid is near its saturation vapor pressure at the walls.

36. A particle condensation apparatus, comprising:
an *apparatus* inlet [receiving] *adapted to receive* an aerosol flow;
a preconditioner [having] *coupled to the apparatus inlet and having walls adapted to cool to* a first temperature [and being coupled to the inlet], the preconditioner having an outlet; and
a condenser *having an interior coupled only* to the outlet and [receiving] *adapted to receive* the aerosol flow from the preconditioner, the *interior of the* condenser [having] *defined by* interior walls [provided at] *adapted to be wetted and heat to* a second temperature higher than the first temperature [and including] *thereby creating* a condensing vapor having a vapor pressure at the interior walls which is near saturation.

38. The [method] *particle condensation apparatus* of claim 36 wherein the condensing vapor is water.

39. The [method] *particle condensation apparatus* of claim 36 wherein the condensing vapor is methanol.

40. The particle condensation apparatus of claim 36 further including a particle-free sheath flow inlet *adapted to surround* the apparatus *inlet*.

41. The [particle condensation apparatus] *method* of claim [40] *53* wherein the first temperature and a vapor pressure of the particle-free sheath flow are controlled by the preconditioner.

42. The particle condensation apparatus of claim 36 wherein the [first temperature and a vapor pressure of the particle-laden flow are controlled by] *walls of* the preconditioner *are adapted to be wetted*.

43. The particle condensation apparatus of claim 40 wherein [a temperature of the particle-free sheath flow is controlled by the preconditioner] *the walls of the preconditioner are adapted to be wetted*.

44. The [particle condensation apparatus] *method* of claim [36] *49* wherein a temperature of the particle-laden flow is controlled by [the] *a* preconditioner.

45. The [particle condensation apparatus] *method* of claim [40] *53* wherein the particle-free sheath flow is air.

46. The [particle condensation apparatus] *method* of claim [40] *53* wherein the particle-free sheath flow is nitrogen.

49. A *method of operating a* particle condensation apparatus, comprising:
[an air inlet receiving] *conditioning* a particle laden airflow *provided to an input of a condenser to a first temperature*; and
[a condenser] *operating the condenser to provide a laminar flow within the condenser, the condenser* having interior walls [provided at] *being heated to* a second temperature higher than [a] *the first* temperature *of the airflow into the condenser and* [having] *maintaining the walls with* a wet surface.

50. The [particle condensation apparatus] *method* of claim 49 wherein the second temperature is 15° C. or greater than the first temperature.

51. The [particle condensation apparatus] *method* of claim 49 wherein the second temperature is 25° C. or greater than the first temperature.

52. The [particle condensation apparatus] *method* of claim 49 wherein the second temperature is 45° C. or greater than the first temperature.

53. The [particle condensation apparatus] *method* of claim 49 [further including] *wherein said conditioning includes surrounding the particle laden airflow with* a particle-free sheath flow [inlet to the apparatus] *prior to the input of the condenser*.

54. The [particle condensation apparatus] *method* of claim 53 wherein the particle free sheath flow is at least 15° C. lower than the second temperature.

55. The [particle condensation apparatus] *method* of claim 53 wherein the particle free sheath flow is at least 25° C. lower than the second temperature.

56. The [particle condensation apparatus] *method* of claim 53 wherein the particle free sheath flow is at least 35° C. lower than the second temperature.

57. The [particle condensation apparatus] *method* of claim [36] *49* further including *providing an output of the condenser to* an optical device for detecting particulate exiting the condenser.

58. The [particle condensation apparatus] *method* of claim [36] *49* further including *providing an output of the condenser to* a droplet collection device.

\* \* \* \* \*